United States Patent [19]
Wind

[11] Patent Number: 5,477,581
[45] Date of Patent: Dec. 26, 1995

[54] DENTAL PROPHYLAXIS INSTRUMENT WIPER

[76] Inventor: Denise A. Wind, 530 Dubois Ave., Valley Stream, N.Y. 11581

[21] Appl. No.: 406,716

[22] Filed: Mar. 20, 1995

[51] Int. Cl.⁶ .................................................. B08B 11/00
[52] U.S. Cl. ...................... 15/210.1; 15/218.1; 15/220.4
[58] Field of Search .................................. 15/210.1, 218, 15/218.1, 220.4, 221, 209.1

[56] References Cited

U.S. PATENT DOCUMENTS

| | | | |
|---|---|---|---|
| 4,752,983 | 6/1988 | Grieshaber | 15/220.4 |
| 4,996,800 | 3/1991 | Mangus | 15/220.4 |

FOREIGN PATENT DOCUMENTS 267694  3/1927  United Kingdom ...................... 15/218

*Primary Examiner*—Edward L. Roberts, Jr.
*Attorney, Agent, or Firm*—Donald Diamond

[57] ABSTRACT

A device for repetitively cleaning the tips, edges and blades of dental instruments during prophylaxis. A first embodiment includes two substantially parallel, contiguous rolls made from a rough, absorbent material and attached to an adhesive strip including a lower surface which adhesively attaches to a dental tray. Second, third and fourth embodiments include, respectively, three, four and five substantially parallel, contiguous rolls.

18 Claims, 2 Drawing Sheets

5,477,581

DENTAL PROPHYLAXIS INSTRUMENT WIPER

BACKGROUND OF THE INVENTION

1. Field of the Invention

The present invention relates to the field of dental hygiene and more particularly to dental prophylaxis procedure.

2. Description of the Related Art

A principal task of all dental hygienists and many dentists is giving patients a dental prophylaxis. Dental prophylaxis is the cleaning of teeth by first scraping away built-up plaque, tartar and calculus, and then polishing the teeth surfaces. Prophylaxis is routinely performed to enhance the appearance of a patient's teeth and also impede reformation of plaque and calculus.

The dental prophylaxis procedure requires utilizing various dental instruments, some of which are pointed and extremely sharp. During a prophylaxis, these instruments are continually being coated with blood and debris, so that the dental care provider must frequently wipe the instruments to clean them.

One method presently used to clean instruments is simply to wipe them on the patient's bib. Not only is this method unprofessional and messy, it is also potentially hazardous to the patient because a careless motion could result in a sharp point penetrating the bib and puncturing the skin. A second method is to wipe instruments on a pile of tissue or cotton placed on a tray. This method is not widely used because contact between an instrument and the tissue or cotton sufficient to ensure adequate cleaning of both edges of the instrument cannot be easily or reliably achieved. Increasing instrument tip pressure against the pile generally results in the unsecured pile sliding over the tray surface. In a third method the dental care provider holds cotton balls, tissue, or gauze pads in the palm of one hand while probing the patient's mouth with an instrument held in the other. This method presently is in widest use because the provider can quickly and efficiently clean instruments. However, the method is potentially hazardous to the provider because he or she risks a puncture wound as well as the invasion of life threatening or otherwise harmful viruses and bacteria. The Center for Disease Control has recommended that this method be discontinued, but has yet to propose a substitute method.

OBJECTS OF THE INVENTION

Accordingly, it is a primary object of the present invention to provide a method for repetitively cleaning dental instruments during a prophylaxis procedure which eliminates the possibility of nicking or puncturing a patient while a dental care provider cleans an instrument.

Another object of the invention is to provide a method for repetitively cleaning dental instruments during a prophylaxis procedure which eliminates the possibility of nicking or puncturing the provider.

A further object of the invention is to provide a device for repetitively cleaning dental instruments during a prophylaxis procedure that is simple, reliable, and easy to use.

Yet another object of the invention is to provide a device that is simple and inexpensive to manufacture.

Other objects of the invention will become evident when the following description is considered with the accompanying drawings.

SUMMARY OF THE INVENTION

The above and other objects are met by the present invention, a device which includes a generally planar array of substantially parallel cylindrical rolls of a material absorbent to blood and other fluids such as cotton, foam or gauze, wherein contiguous pairs of rolls are attached along their tangent lengths so as to form a cusp-shaped crevice or groove between and along each pair of contiguous rolls. The rolls are rigidly attached to the upper surface of a planar adhesive strip. A roll surface has a relatively rough and porous texture rather than a smooth and nonporous texture, and the rolls are sufficiently firm to resist deflection from a pressure or force such as may be applied by the tip, edge or blade of a dental instrument. The lower surface of the adhesive strip is covered by a peel-off strip which, when removed, exposes adhesive on the lower surface which serves to securely attach the device to a metal, porcelain or plastic surface.

Each device is packaged in a sterile wrapper, similar to packaging used for adhesive bandages. Before beginning work on a patient, the provider removes a device from its wrapper, peels off the protective strip, and adhesively attaches the device to a dental tray. As an instrument becomes fouled with blood, saliva and debris particles while work proceeds on the patient, the provider wipes the instrument tip on the roll surfaces as often as needed to keep the tip clean. An instrument having a sharp blade or edge is cleaned by sliding the instrument head one or several times through an inter-roll crevice, the process being similar to a knife blade being pulled through a sharpener.

A first preferred embodiment includes two rolls made from a stiff absorbent foam, stiff gauze, or tightly-rolled cotton. A second preferred embodiment includes three rolls made from cotton or linen. A third preferred embodiment includes four rolls made from tightly-rolled cotton. A fourth preferred embodiment includes five rolls made from a stiff absorbent foam, tightly-rolled cotton, or linen.

A more complete understanding of the present invention and other objects, aspects and advantages thereof will be gained from a consideration of the following description of the preferred embodiments read in conjunction with the accompanying drawings provided herein.

DESCRIPTION OF THE PREFERRED EMBODIMENT

I. INTRODUCTION

Figure 1:
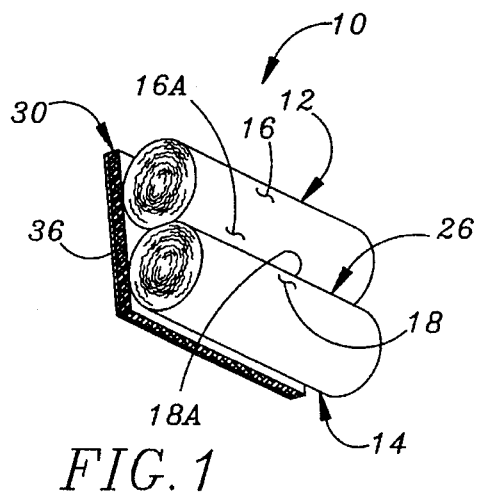
FIG. 1 is a perspective view of a first preferred embodiment.
Figure 1A:
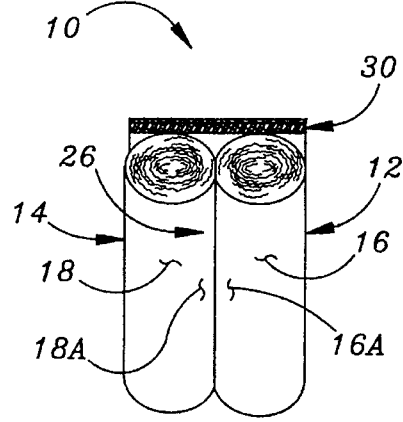
FIG. 1a is a top perspective view of the FIG. 1 embodiment.
Figure 2:
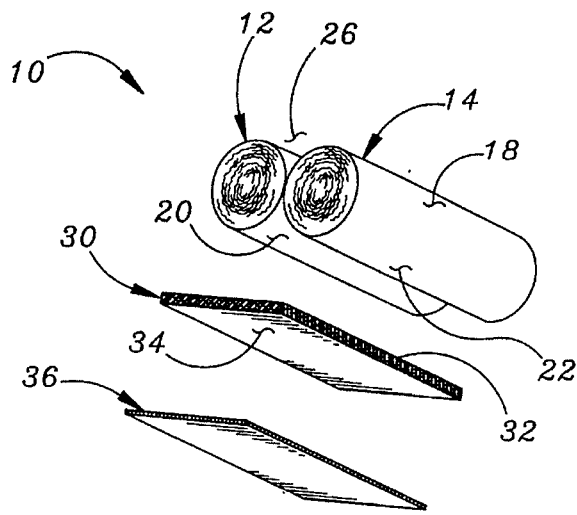
FIG. 2 is an exploded perspective view of the FIG. 1 embodiment.

While the present invention is open to various modifications and alternative constructions, the preferred embodiments shown in the drawings will be described herein in detail. It is to be understood, however, there is no intention to limit the invention to the particular forms disclosed. On the contrary, it is intended that the invention cover all modifications, equivalences and alternative constructions falling within the spirit and scope of the invention as expressed in the appended claims.

II. FIRST PREFERRED EMBODIMENT

Figure 3:
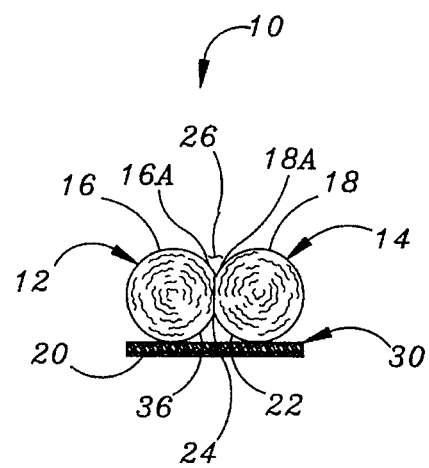
FIG. 3 is an end elevational view of the FIG. 1 embodiment.

Referring to FIGS. 1, 1a, 2 and 3, a device 10 according to a first embodiment includes first and second generally cylindrical rolls 12 and 14 having a convexly-shaped upper surface 16, 18, respectively, and a convexly-shaped lower surface 20, 22, respectively, the surfaces 16, 20 and 18, 22 determined with respect to a common generally horizontal median plane. Upper surfaces 16, 18 include along the roll length an interior portion 16A, 18A, respectively. In any particular device sample, rolls 12, 14 are fabricated from the same material and have generally the same length and diameter. As best shown in FIG. 3, the rolls are transversely compressed and rigidly connected along their lengths in an interface area 24 generally orthogonal to and symmetric about the median plane, so as to form a cusp-shaped crevice (or groove) 26. The device 10 further includes a generally planar adhesive strip 30 including an upper adhesive surface 32 and a lower adhesive surface Surfaces 20, 22 of rolls 12, 14, respectively, are rigidly attached to the surface 32. A peel-off strip 36 is attached to the adhesive surface 34. Removing strip 36 from surface 34 exposes the adhesively coated surface 34.

The rolls generally have a common length in a range from about 1-inch to about 3-inches, and a common diameter in a range from about ⅛-inch to about 1-inch. In one embodiment, the rolls 12, 14 are each about 1-inch long and about ¼-inch diameter, and are made from a stiff absorbent foam having a porous, rough surface texture such as open-celled urethane, or from tightly-rolled cotton such as is commonly used in dentistry. Alternatively, the rolls are each about 2-inches long and about ½-inch diameter, and are made from the stiff absorbent foam. Alternatively, the rolls are each about 3-inches long and about ½-inch diameter, and are made from a stiff gauze. Regardless of the material used to fabricate the rolls, the rolls are sufficiently firm to resist deflection from a downward pressure such as may be applied by the tip of a dental instrument or from a lateral force tending to increase separation between interior surface portions 16A, 18A as the blade or edge of a dental instrument is drawn through the crevice 26.

III. SECOND PREFERRED EMBODIMENT

Figure 4:
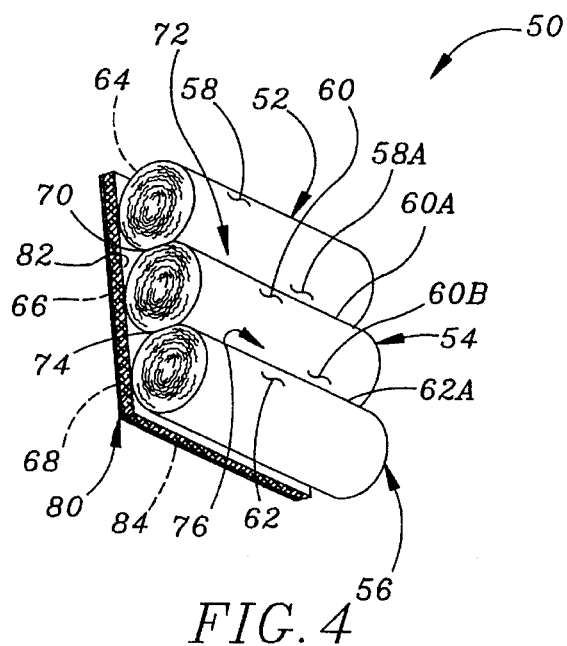
FIG. 4 is a perspective view of a second embodiment.

Referring to FIG. 4, a device 50 according to a second embodiment includes first, second and third generally cylindrical rolls 52, 54 and 56 having convexly-shaped upper surfaces 58, 60, 62, respectively, and convexly-shaped lower surfaces 64, 66, 68, respectively, wherein the surfaces 58, 64, and 60, 66, and 62, 68, are determined with respect to a common generally horizontal median plane. Upper surfaces 58, 60, 62 include along the roll length interior portions 58A, 60A and 60B, and 62A, respectively. In any particular device sample, the rolls 52, 54, 56 are fabricated from the same material and have generally the same length and diameter. Similar to the first embodiment, the rolls are transversely compressed and contiguous rolls are rigidly connected along their tangent lengths to form a cusp-shaped crevice. Thus, rolls 52 and 54 are connected along an interface 70 to form a crevice 72 between interior surface portions 58A and 60A, and rolls 54 and 56 are connected along an interface 74 to form a crevice 76 between interior surface portions 60B and 62A. The device 50 further includes a generally planar adhesive strip 80 including an upper adhesive surface 82 and a lower adhesive surface 84. Surfaces 64, 66, 68 of rolls 52, 54, 56, respectively, are rigidly attached to the surface 82. A peel-off strip 86 (not shown) is attached to the adhesive surface 84. Removing strip 86 from surface 84 exposes the adhesively coated surface 84.

In one construction, the rolls 52, 54, 56 are each about 1-inch long and about 1-inch diameter, and are made from stiff cotton. Alternatively, the rolls 52, 54, 56 are each about 3-inches long and about ¾-inch diameter, and are made from linen. Regardless of the material used to fabricate the rolls, the rolls are sufficiently firm to resist deflection from a downward pressure such as may be applied by the tip of a dental instrument or from a lateral force tending to increase separation between interior surface portions 58A, 60A, or 60B, 62A as the blade or edge of a dental instrument is drawn through crevice 72 or 76, respectively.

IV. THIRD PREFERRED EMBODIMENT

Figure 5:
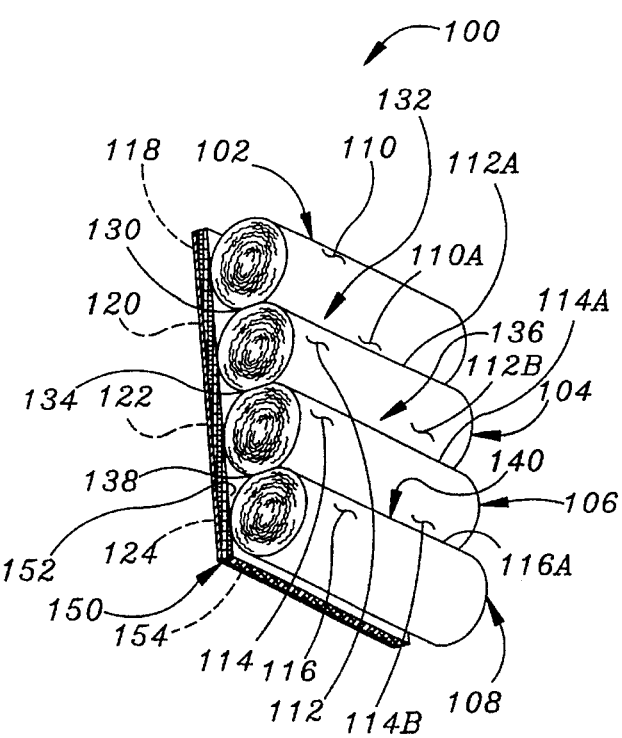
FIG. 5 is a perspective view of a third embodiment.

Referring to FIG. 5, a device 100 according to a third embodiment includes first, second, third and fourth generally cylindrical rolls 102, 104, 106, 108 having convexly-shaped upper surfaces 110, 112, 114, 116, respectively, and convexly-shaped lower surfaces 118, 120, 122, 124, respectively, wherein the surfaces 110, 118, and 112, 120, and 114, 122, and 116, 124, are determined with respect to a common generally horizontal median plane. Upper surfaces 110, 112, 114, 116 include along the roll length interior portions 110A, 112A and 112B, 114A and 114B, and 116A, respectively. In any particular device sample, the rolls 102, 104, 106, 108 are fabricated from the same material and have generally the same length and diameter. Similar to the first embodiment, the rolls are transversely compressed and contiguous rolls are rigidly connected along their tangent lengths to form a cusp-shaped crevice. Thus, rolls 102 and 104 are connected along an interface 130 to form a crevice 132, rolls 104 and 106 are connected along an interface 134 to form a crevice 136, and rolls 106 and 108 are connected along an interface 138 to form a crevice 140. The device 100 further includes a generally planar adhesive strip 150 including an upper adhesive surface 152 and a lower adhesive surface 154. Surfaces 118, 120, 122, 124 of rolls 102, 104, 106, 108, respectively, are rigidly attached to the surface 152. A peel-off strip 160 (not shown) is attached to the adhesive surface 154. Removing strip 160 from surface 154 exposes the adhesively-coated surface 154.

In an illustrative construction, the rolls 102, 104, 106, 108 are each about 2½ inches long and about 1-inch diameter, and are made from tightly-rolled cotton. The rolls are sufficiently firm to resist deflection from a downward pressure such as may be applied by the tip of a dental instrument or from a lateral force tending to increase separation between interior surface portions 110A, 112A, or 112B, 114A, or 114B, 116A, as the blade or edge of a dental instrument is drawn through crevice 132, 136, or 140, respectively.

V. FOURTH PREFERRED EMBODIMENT

Figure 6:
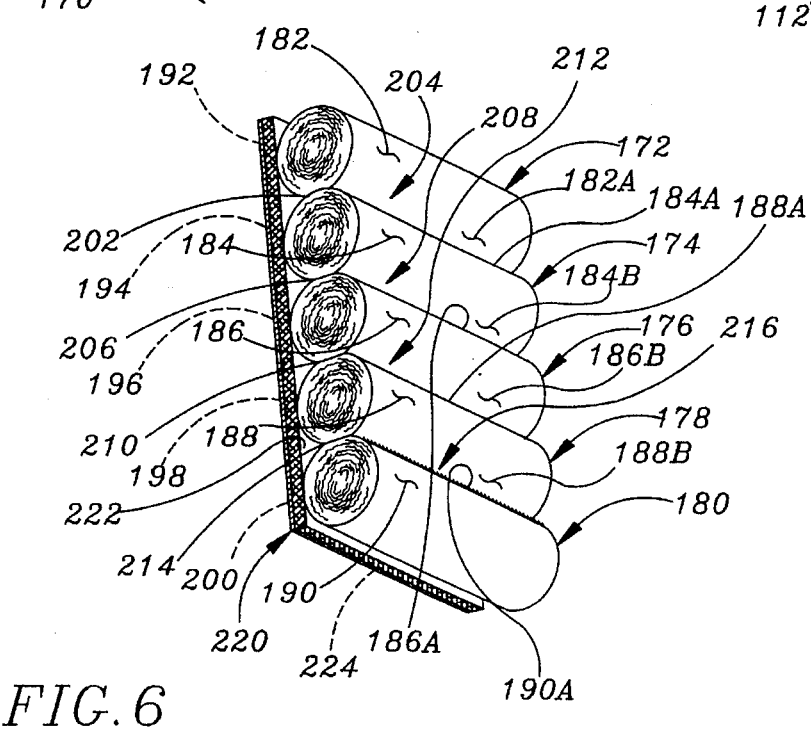
FIG. 6 is a perspective view of a fourth embodiment.

Referring to FIG. 6, a device 170 according to a fourth embodiment includes first, second, third, fourth and fifth generally cylindrical rolls 172, 174, 176, 178, 180 having convexly-shaped upper surfaces 182, 184, 186, 188, 190 respectively, and convexly-shaped lower surfaces 192, 194, 196, 198, 200, respectively, wherein the surfaces 182, 192, and 184, 194, and 186, 196, and 188, 198, and 190, 200, are determined with respect to a common generally horizontal median plane. Upper surfaces 182, 184, 186, 188, 190 include along the roll length interior portions 182A, 184A and 184B, 186A and 186B, 188A and 188B, and 190A, respectively. In any particular device sample, the rolls 172, 174, 176, 178, 180 are fabricated from the same material and have generally the same length and diameter. Similar to the first embodiment, the rolls are transversely compressed and contiguous rolls are rigidly attached along their tangent lengths to form a cusp-shaped crevice. Thus, rolls 172 and 174 are connected along an interface 202 to form a crevice 204, rolls 174 and 176 are connected along an interface 206 to form a crevice 208, rolls 176 and 178 are connected along an interface 210 to form a crevice 212, and rolls 178 and 180 are connected along an interface 214 to form a crevice 216. The device 170 further includes a generally planar adhesive strip 220 including an upper adhesive surface 222 and a lower adhesive surface 224. Surfaces 192, 194, 196, 198, 200 of rolls 172, 174, 176, 178, 180, respectively, are rigidly attached to the surface 222. A peel-off strip 230 (not shown) is attached to the adhesive surface 224. Removing strip 230 from surface 224 exposes the adhesively-coated surface 224.

In one construction, the rolls 172, 174, 176, 178, 180 are each about 3-inches long and about ⅛-inch diameter, and are made from a stiff absorbent foam, tightly-rolled cotton, or linen. The rolls are sufficiently firm to resist deflection from a downward pressure such as may be applied by the tip of a dental instrument or from a lateral force tending to increase separation between interior surface portions 182A, 184A, or 184B, 186A, or 186B, 188A, or 188B, 190A, as the blade or edge of a dental instrument is drawn through crevice 204, 208, 212, or 216, respectively.

VI. METHOD OF USE

To use the device 10, 50, 100, or 170, a dental care provider, before beginning work on a patient, removes the device from its protective wrapper, peels off the strip 36, 86, 160, 230, respectively, and presses the adhesive surface 34, 84, 154, 224, respectively, onto the surface of a dental tray so that the device is firmly attached to the tray. Typically, the tray is made from porcelain, aluminum or stainless steel. While working on the patient's mouth with a dental instrument, as the instrument becomes fouled with blood, saliva and debris, the provider cleans the instrument by wiping its tip on the upper roll surfaces and/or sliding a fouled blade or edge one or more times through the cusp-shaped crevice between two contiguous rolls.

What is claimed is:

1. A device for cleaning dental instruments comprising:
 a plurality of substantially parallel, generally cylindrical rolls, serially contiguous, each roll having a substantially common predetermined length and a substantially common diameter and fabricated from a common material, each roll having a convexly-shaped-upper surface and a convexly-shaped lower surface determined with respect to a common generally horizontal median plane, each pair of contiguous rolls connected lengthwise along an interface area generally orthogonal to and symmetric about the median plane, thereby forming between each pair of contiguous rolls a cusp-shaped crevice bounded by an interior portion of each upper surface;
 a generally planar adhesive strip having an upper adhesive surface and a lower adhesive surface, a lengthwise portion of the lower surface of each roll rigidly attached to the strip upper surface; and
 a peel-off strip attached to the strip lower surface.

2. The device of claim 1, wherein said common length is in a range of about 1-inch to about 3-inches, and said common diameter is in a range of about ⅛-inch to about 1-inch.

3. The device of claim 2, wherein said common material is selected from the group consisting of a stiff absorbent foam, tightly rolled cotton, stiff cotton, a stiff gauze, and linen.

4. The device of claim 1, wherein said plurality of rolls is two.

5. The device of claim 4, wherein said common length is about 1-inch and said common diameter is about ¼-inch.

6. The device of claim 5, wherein said common material is selected from the group consisting of a stiff absorbent foam and tightly-rolled cotton.

7. The device of claim 4, wherein said common length is about 2-inches and said common diameter is about ½-inch.

8. The device of claim 7, wherein said common material is a stiff, absorbent foam.

9. The device of claim 4, wherein said common length is about 3-inches and said common diameter is about ½-inch.

10. The device of claim 9, wherein said common material is a stiff gauze.

11. The device of claim 1, wherein said plurality of rolls is three.

12. The device of claim 11, wherein said common length is about 1-inch, said common diameter is about 1-inch, and said common material is stiff cotton.

13. The device of claim 11, wherein said common length is about 3-inches, said common diameter is about ¾-inch, and said common material is linen.

14. The device of claim 1, wherein said plurality of rolls is four.

15. The device of claim 14, wherein said common length is about 2½ inches, said common diameter is about 1-inch, and said common material is tightly-rolled cotton.

16. The device of claim 1, wherein said plurality of rolls is five.

17. The device of claim 16, wherein said common length is about 3-inches and said common diameter is about ⅛-inch.

18. The device of claim 17, wherein said common material is selected from the group consisting of a stiff absorbent foam, tightly-rolled cotton, and linen.

\* \* \* \* \*